United States Patent [19]

Otake et al.

[11] Patent Number: 4,472,527

[45] Date of Patent: Sep. 18, 1984

[54] PROCESS FOR PREPARING AN OXIDATION CATALYST COMPOSITION

[75] Inventors: Masayuki Otake; Masayoshi Murayama; Yuji Kawaragi, all of Yokohama, Japan

[73] Assignee: Mitsubishi Chemical Industries Ltd., Tokyo, Japan

[21] Appl. No.: 473,196

[22] Filed: Mar. 8, 1983

[30] Foreign Application Priority Data

| Mar. 31, 1982 | [JP] | Japan | 57-52645 |
| Apr. 1, 1982 | [JP] | Japan | 57-54502 |
| May 4, 1982 | [JP] | Japan | 57-74920 |
| Nov. 17, 1982 | [JP] | Japan | 57-201728 |
| Nov. 19, 1982 | [JP] | Japan | 57-203370 |
| Nov. 22, 1982 | [JP] | Japan | 57-205255 |

[51] Int. Cl.$^3$ .................................. B01J 27/14
[52] U.S. Cl. .................... 502/209; 502/210; 502/214; 549/259; 549/260
[58] Field of Search .................... 252/435, 437

[56] References Cited

U.S. PATENT DOCUMENTS

| 3,293,268 | 12/1966 | Bergman et al. | 252/437 X |
| 4,111,963 | 9/1978 | Mount et al. | 252/437 X |
| 4,209,423 | 6/1980 | Hutchings et al. | 252/435 |
| 4,283,288 | 8/1981 | Udovich et al. | 252/437 |
| 4,328,120 | 5/1982 | Udovich | 252/437 X |
| 4,328,126 | 5/1982 | Udovich et al. | 252/437 X |
| 4,351,773 | 9/1982 | Milberger et al. | 252/437 |
| 4,371,702 | 2/1983 | Bither, Jr. | 252/437 X |
| 4,374,756 | 2/1983 | Harju et al. | 252/437 X |

FOREIGN PATENT DOCUMENTS

| 7308517 | 7/1973 | Netherlands | 252/437 |
| 1285075 | 8/1972 | United Kingdom | 252/437 |

OTHER PUBLICATIONS

English Abstract of Jap. unexamined Patent Pub. Nos. 126587/1974; 8788/1975;33038/1975;65635/1981;95990/1976;45815/-1981.

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

A process for preparing an oxidation catalyst composition comprises mixing at least one crystalline composite oxide, as the first component, selected from the group consisting of (i) a crystalline composite oxide containing vanadium and phosphorus and showing the characteristic X-ray diffraction peaks as identified in the following Table A and (ii) a crystalline composite oxide containing vanadium and phosphorus and showing the characteristic X-ray diffraction peaks as identified in the following Table B, an aqueous solution, as the second component, containing vanadium and phosphorus, and silica sol, as the third component, to form an aqueous slurry, spray-drying the slurry, and calcining the solid particles thereby obtained:

TABLE A

| X-ray diffraction peaks (Anticathode: Cu—K$_\alpha$) 2θ (±0.2°) |
|---|
| 15.7° |
| 19.6° |
| 24.2° |
| 27.1° |
| 28.8° |
| 30.4° |

TABLE B

| X-ray diffraction peaks (Anticathode: Cu—K$_\alpha$) 2θ (±0.2°) |
|---|
| 14.2° |
| 15.7° |
| 18.5° |
| 23.0° |
| 28.4° |
| 30.0° |
| 33.7° |
| 36.8° |

14 Claims, No Drawings

PROCESS FOR PREPARING AN OXIDATION CATALYST COMPOSITION

The present invention relates to a process for preparing an oxidation catalyst composition. More particularly, the present invention relates to a process for preparing an oxidation catalyst composition suitable for use as a catalyst for the production of maleic anhydride by vapour-phase oxidation of a hydrocarbon having at least 4 carbon atoms, especially butane.

It is known that in the process for producing maleic anhydride by vapour-phase oxidation of a hydrocarbon having 4 carbon atoms such as n-butane, n-butenes or butadiene, a composite oxide containing vanadium and phosphorus as the essential components is effective as a catalyst (U.S. Pat. No. 3,293,268). It is further reported that in this catalyst, crystalline vanadyl phosphate (($VO)_2P_2O_7$) is effective as the active component (E. Bordes, P Courtine, J. Catal., 57, 236 (1979)). The crystal phase of this compound can be identified by the characteristic X-ray diffraction pattern as shown in the following Table B:

TABLE B

| X-ray diffraction of $(VO)_2P_2O_7$ (Anticathode Cu—$K_\alpha$), Major peaks | |
|---|---|
| $2\theta$ (±0.2°) | Intensity |
| 14.2° | 20 |
| 15.7° | 20 |
| 18.5° | 20 |
| 23.0° | 100 |
| 28.4° | 90 |
| 30.0° | 50 |
| 33.7° | 40 |
| 36.8° | 40 |

The present inventors have confirmed that when used as a catalyst for vapour-phase oxidation of n-butane, n-butenes and the like, the crystal phase of the compound exhibits substantially higher catalytic activities than those of the amorphous composite oxide catalysts prepared by the conventional processes and particularly when it is used for the oxidation of butane, the reaction proceeds even at a low temperature of about 100° C. Accordingly, it is preferred for the process to use the catalytically active components having the X-ray diffraction peaks as identified in the above Table B.

On the other hand, the vapour-phase oxidation reaction for the formation of maleic anhydride from hydrocarbons having 4 carbon atoms including the side reaction for complete oxidation (i.e. the formation of carbon monoxide and carbon dioxide) is a highly exothermic reaction. Accordingly, from a view-point of energy efficiency as well as from a view-point of a relatively low limiting concentration for the explosion of the hydrocarbon material relative to air, a fluidized bed catalytic oxidation reaction has been believed to be most suitable for the reaction. As a catalyst developed for this purpose, there is a catalyst which has been prepared by spray-drying a mixture comprising a vanadyl oxalate solution, phosphoric acid, silica sol and a suitable activity-promoting ingredient (British Pat. No. 1,285,075). The catalyst thus obtained is effective for the oxidation of butenes and butadiene. However, for the oxidation of butane, its catalytic activity is not high enough and it is usually required that the reaction be conducted at a temperature of at least 500° C.

There have been several reports relating to fluidized bed catalysts useful for the oxidation of butane. For instance, Japanese Unexamined Patent Publication No. 126587/1974 discloses a case where a composite oxide is formed by contacting a pentavalent vanadium compound with a trivalent phosphorus compound, and then the composite oxide is pulverized into fine powder, which is then used for a fluidized bed reaction. In this process, a crystalline active component can be taken out and the catalytic activity can be adequately improved. However, the strength and the flowability of the catalyst are not adequate.

Certain possibilities of the pulverized catalyst fluidized bed reaction in which such fine powder of a catalytically active component is used, are also pointed out in Japanese Unexamined Patent Publications No. 8788/1975 and No. 33038/1981, and a possibility for the production of a fluidized bed catalyst by depositing a complex oxide on a carrier is pointed out in Japanese Unexamined Patent Publication No. 65635/1981.

The present inventors have conducted extensive researches to develop a catalyst useful particularly for the vapour-phase oxidation of n-butane by a fluidized bed and as a result have found that a catalyst having superior strength and flowability can be prepared by mixing a special crystalline oxide, as the first component, containing vanadium and phosphorus, an aqueous solution, as the second component, containing vanadium and phosphorus, silica sol as the third component, to prepare a slurry and spray-drying the slurry. The present invention has been accomplished based on this discovery.

It is an object of the present invention to provide a process for preparing an oxidation catalyst composition suitable for use in the production of maleic anhydride by vapour-phase oxidation of a hydrocarbon having at least 4 carbon atoms.

Another object of the present invention is to provide a process for producing an oxidation catalyst composition suitable for use in the production of maleic anhydride by vapour-phase oxidation of n-butane and n-butenes.

A further object of the present invention is to provide a process for preparing an oxidation catalyst composition for a fluidized bed which has superior strength and flowability and which is suitable for use in an industrial production of maleic anhydride by vapour-phase oxidation of n-butane and n-butenes by means of a fluidized bed reactor.

The present invention provides a process for preparing an oxidation catalyst composition which comprises mixing at least one crystalline composite oxide, as the first component, selected from the group consisting of (i) a crystalline composite oxide containing vanadium and phosphorus and showing the characteristic X-ray diffraction peaks as identified in the following Table A and (ii) a crystalline composite oxide containing vanadium and phosphorus and showing the characteristic X-ray diffraction peaks as identified in the following Table B, an aqueous solution, as the second component, containing vanadium and phosphorus, and silica sol, as the third component, to form an aqueous slurry, spray-drying the slurry, and calcining the solid particles thereby obtained:

TABLE A

| X-ray diffraction peaks (Anticathode: Cu—K$_\alpha$) 2θ (±0.2°) |
| --- |
| 15.7° |
| 19.6° |
| 24.2° |
| 27.1° |
| 28.8° |
| 30.4° |

TABLE B

| X-ray diffraction peaks (Anticathode: Cu—K$_\alpha$) 2θ (±0.2°) |
| --- |
| 14.2° |
| 15.7° |
| 18.5° |
| 23.0° |
| 28.4° |
| 30.0° |
| 33.7° |
| 36.8° |

Now, the present invention will be described in detail with reference to the preferred embodiments.

In the present invention, a crystalline vanadium-phosphorus composite oxide showing the characteristic X-ray diffraction peaks as identified in Table A or B is used as the first component. As mentioned above, the vanadium-phosphorus composite oxide showing the characteristic X-ray diffraction peaks as identified in Table B is known and it is usually prepared by firstly preparing its precursor i.e. a crystalline composite oxide containing tetravalent vanadium and pentavalent phosphorus and showing the characteristic X-ray diffraction peaks as identified in the following Table A (hereinafter referred to as "a precursory oxide") and then calcining the precursory oxide. (The vanadium-phosphorus composite oxide showing the characteristic X-ray diffraction peaks as shown in Table B will be hereinafter referred to as "a calcined oxide".)

TABLE A

| X-ray diffraction peaks (Anticathode Cu—K$_\alpha$) | |
| --- | --- |
| 2θ (±0.2°) | Intensity |
| 15.7° | 100 |
| 19.6° | 50 |
| 24.2° | 40 |
| 27.1° | 45 |
| 28.8° | 25 |
| 30.4° | 80 |

This precursory oxide is known and it can be prepared by the following known methods.

(1) In a non-oxidizing acidic solution such as a hydrochloric acid solution, a pentavalent vanadium such as vanadium pentoxide is dissolved and reduced, the reduction being completed by a reducing agent such as oxalic acid to obtain a solution containing tetravalent vanadium ions, the solution is reacted with phosphoric acid and a soluble vanadium-phosphorus composite thereby formed is precipitated by an addition of water (Japanese Unexamined Patent Publication No. 95990/1976).

(2) A pentavalent vanadium compound such as vanadium pentoxide and phosphoric acid are reacted in an aqueous medium in the presence of a reducing agent such as hydrazine hydrochloride or a hydroxylamine hydrochloride, followed by concentration or evaporation to obtain crystals (Japanese Unexamined Patent Publication No. 45815/1981).

(3) Vanadium pentoxide is reduced in an organic medium such as ethanol, isopropanol or glycerol and then reacted with anhydrous phosphoric acid, and water is azeotropically removed with use of a solvent such as benzene, whereby crystals are precipitated (U.S. Pat. No. 4,283,288).

Further, some of the present inventors have proposed a method for preparing the precursory oxide showing the characteristic X-ray diffraction peaks as identified in the above Table A by subjecting an aqueous solution containing pentavalent phosphorus and tetravalent vanadium to hydrothermal treatment at a temperature of from 110° to 250° C. (Japanese patent application No. 32110/1982). In this method, firstly a pentavalent vanadium compound such as vanadium pentoxide is reacted with phosphoric acid in an aqueous acidic medium containing a halogen-free reducing agent such as hydrazine hydrate to obtain an aqueous solution containing tetravalent vanadium and phosphoric acid as major components and then the aqueous solution is subjected to hydrothermal treatment in a closed container at a temperature of from 110° to 250° C., preferably from 120° to 180° C. for about 0.5 to 200 hours. As the aqueous medium, water is usually used. A hydrophilic organic solvent such as an alcohol, a carboxylic acid, an ether or a ketone may optionally be combined with water. However, the reducing rate of vanadium is thereby reduced, and accordingly, the amount of such a hydrophilic organic solvent should be at most 50% by weight. The phosphoric acid concentration in the aqueous medium is usually from 5 to 50% by weight, preferably from 5 to 35% by weight. If the phosphoric acid concentration is too high, it is possible that vanadium pentoxide reacts with phosphoric acid before it is reduced and the viscosity of the solution tends to be extremely high, whereby the handling becomes difficult. The reduction can adequately be done with use of the reducing agent in a stoichiometric amount required for reducing the pentavalent vanadium to the tetravalent vanadium, and the reducing agent is usually used in an amount within a range of from 95 to 120% of the stoichiometric amount. As the reducing agent, a non-halogen inorganic reducing agent such as hydrazine, hydroxylamine or a phosphate thereof is preferably used. If desired, an organic reducing agent such as oxalic acid may be used, but the use of such an organic reducing agent is not industrially advantageous. The reduction of vanadium is conducted preferably by a method which comprises adding vanadium pentoxide to an aqueous solution which has previously been prepared by dissolving phosphoric acid and the reducing agent, whereby it is possible to form crystals having higher purity. At the time of the hydrothermal treatment, it is preferred to add a small amount of finely pulverized seed crystals to the aqueous solution. By such hydrothermal treatment, a slurry containing grayish blue fine crystals is obtained. These crystals are the desired precursory oxide, and they are obtainable by evaporating or spray-drying the slurry or directly from the slurry by solid-liquid separation such as filtration. By this method, it is possible to obtain the oxide having finer particle sizes than those obtainable by the above-mentioned conventional methods.

The precursory oxide obtainable by the foregoing methods may be represented by the formula $(V_2O_4)$(-

$P_2O_5)(2H_2O)$. Thus, the atomic ratio of phosphorus to vanadium (P/V) is theoretically 1.0. Practically, however, when any one of the above-mentioned methods is used, the vanadium compound and the phosphorus compound are preferably reacted in a P/V atomic ratio within a range of from 0.8 to 1.25.

Further, in the first component to be used for the process of the present invention, a part of the vanadium atoms may be substituted by various metal atoms having an ion radius not very much different from the vanadium ions. As such metals, there may be mentioned iron, chromium, aluminum, titanium, cobalt, magnesium, manganese and nickel. When used for a catalyst, the composite oxide partly substituted by such metal atoms brings about a remarkable improvement in the catalytic activity and the stability of the catalytic activity. The proportion of the substitution is optionally selected within a range of from 0.005 to 0.4 mol, preferably from 0.05 to 0.2 mol of the metal atoms per mol of vanadium atoms. As a method for introducing such other metal atoms to the composite oxide, there may be mentioned a method wherein these metal ions are added in the form of an inorganic salts such as a chloride, a hydroxide, a sulfate, a nitrate or a carbonate, or an organic salt such as an oxalate during the process for preparing the precursory oxide.

The X-ray diffraction pattern of the substituted solid solution-type precursory oxide thus obtained is more or less shifted from the peaks shown in Table A. However, degree of the shift is within a range of $\pm 0.2°$.

The precursory oxide is then calcined in an atmosphere of an inert gas such as argon or nitrogen, whereby the above-mentioned calcined oxide is obtained. In the calcined oxide, vanadium is present substantially in its tetravalent state. It is preferred to calcine it in air to convert a part of vanadium to its pentavalent state. The ratio of the pentavalent vanadium to the total vanadium in the calcined oxide is inter-related with the properties of the catalysts finally obtained. In general, the best results are obtainable when the ratio of the pentavalent vanadium is within a range of from 15 to 25%. The properties will be degraded if the ratio is greater or smaller than this range. And, if the ratio of the pentavalent vanadium exceeds 35%, the crystal phase showing the above characteristic X-ray diffraction peaks (i.e. the crystal phase of $(VO)_2P_2O_7$) tends to undergo decomposition. Such an excessively oxidized calcined oxide has a disadvantage that it sometimes forms a rubber-like solid substance during the preparation of the catalyst and the catalyst thereby obtained tends to have poor properties. Accordingly, the calcination in air should be conducted within a range where the ratio of the pentavalent vanadium is at most 35%. The preferred ratio of the pentavalent vanadium in the calcined oxide is from 5 to 35%.

Instead of the two step calcination with the inert gas and air, it is possible to calcine the above-mentioned precursory oxide in air diluted with an inert gas to obtain a calcined oxide containing the pentavalent vanadium in a predetermined ratio. In the case where the calcined oxide is prepared by calcining the precursory oxide in ordinary air, it is necessary to take a precaution not to excessively oxidize the vanadium, for instance, by controlling the temperature.

The calcination of the precursory oxide may be conducted in a furnace of any optional type. However, it is usual to use a muffle furnace, a rotary kiln or a fluidized bed calcination furnace. The calcination temperature is usually higher than the dehydration temperature of the precursory oxide i.e. from 430° to 700° C., preferably from 450° to 600° C.

As mentioned above, the precursory oxide is separated from a slurry containing it by means of solid-liquid separation such as filtration or evaporation or spray-drying, and if required, it is further calcined to form a calcined oxide before using it as the first component. Further, in the case where the above-mentioned hydrothermal treatment is used, it is not indispensable to separate the precursory oxide from the slurry and it may be used by itself as the first component. In this case, it is possible that phosphoric acid, a reducing agent and vanadium pentoxide are added and dissolved in the slurry and the liquid phase thereby obtained is used as the second component. Further, it is also possible that phosphoric acid, a reducing agent and vanadium pentoxide are added and dissolved in a liquid phase obtained by solid-liquid separation of the slurry after the hydrothermal treatment and the solution thereby obtained is used as the second component.

As mentioned above, the first component may be used in the form of either the precursory oxide or the calcined oxide. However, it is preferred to use it in the form of the calcined oxide from the view-points of the strength and catalytic activities of the catalyst. Further, for the strength of the catalyst finally obtained, the first component should preferably be in the form of fine particles having an average particle size of at most 10 μm, especially at most 5 μm, as measured by a Coulter counter method. Accordingly, it is preferably pulverized at the stage of the precursory oxide or at the stage of the calcined oxide. According to the above-mentioned hydrothermal treatment, the fine precursor oxide can be formed. Accordingly, when the slurry obtained by the hydrothermal treatment and containing the fine precursory oxide, is spray-dried, small agglomerates of a precursory oxide having the above-mentioned size can directly be obtained. For the pulverization, a conventional dry-type or wet-type pulverizer such as a hammer mill, a jet mill, a colloid mill or a sand grinder may be used. In the case of the wet-type pulverization, the first component may be mixed with the second component and/or the third component prior to the pulverization operation.

The aqueous solution containing vanadium and phosphorus as the second component of the present invention usually contains substantially tetravalent vanadium and pentavalent phosphorus and it is preferred that at least a part thereof is present in the form of vanadyl phosphate.

This second compartment serves as a binder for the composite oxide of the first component and the silica sol of the third component as a carrier, and thus it contributes to an improvement of the flowability and the strength of the fluidized bed catalyst. The method for preparing such an aqueous solution is not critical. Some examples for the preparation will be given below.

It is usually prepared by adding and dissolving a reducing agent and vanadium pentoxide in an aqueous solution containing a phosphoric acid. The atomic ratio of phosphorus to vanadium in the aqueous solution is preferably within a range of from 0.5 to 10. In general, the aqueous solution containing vanadyl phosphate is unstable and it is often difficult to maintain the solution stably for a long period of time. In order to stabilize the aqueous solution, oxalic acid may be added. The amount of the addition is such that the molar ratio of oxalic acid to the vanadium element is at most 1.2, preferably within a range of from 0.2 to 1. If the amount of oxalic acid is excessive, it adversely affects the mechanical strength, the bulk density and the catalytic activities of the catalyst. In other words, the range of the molar ratio of oxalic acid to vanadium element being at most 1.2 corresponds to the range within which no vanadyl oxalate is formed. Specific examples for the preparation of the aqueous solution are as follows.

In the first method, vanadium pentoxide is added to an aqueous solution containing phosphoric acid and oxalic acid in such an amount that the molar ratio of oxalic acid to vanadium element is at most 1.7 and preferably at least 0.7, whereby an aqueous solution containing vanadyl phosphate and oxalic acid is obtained. More specifically, oxalic acid is dissolved in an aqueous acidic medium containing phosphoric acid, and vanadium pentoxide is added while the temperature is maintained by slight heating at a level where the reduction proceeds. According to this method, after the completion of the reduction, oxalic acid will be present in an amount of at most 1.2 mol relative to the vanadium element.

In the second method, a reducing agent other than oxalic acid, preferably at least one of the reducing agents selected from inorganic reducing agents such as hydrazine hydrate or hydrochlorides and phosphates of hydrazine or hydroxylamine and organic reducing agents such as lactic acid, is added to an aqueous acidic solution containing phosphoric acid, and then vanadium pentoxide is added, whereby the reduction is conducted to obtain a uniform aqueous solution containing vanadyl phosphate. Thereafter, oxalic acid is preferably added.

In the third method, vanadium pentoxide, phosphoric acid and phosphorous acid were mixed in an aqueous medium, whereby tetravalent vanadium ions are formed by the reducing agent of the phosphorous acid. When the aqueous solution containing vanadyl phosphate obtained by this method, is left to stand, crystalline solid substance showing the characteristic X-ray diffraction peaks as identified in the following Table C is precipitated.

TABLE C

| | (Anticathode Cu—$K_\alpha$) | | |
|---|---|---|---|
| $2\theta$ (±0.2°) | Intensity | $2\theta$ (±0.2°) | Intensity |
| 11.0° | 100 | 26.2° | 10 |
| 12.1° | 20 | 28.2° | 20 |
| 14.4° | 10 | 29.2° | 15 |
| 15.4° | 10 | 29.5° | 10 |
| 17.1° | 10 | 31.0° | 25 |
| 21.6° | 15 | 37.5° | 10 |
| 22.3° | 40 | 48.5° | 10 |
| 22.7° | 10 | 49.7° | 15 |

The precipitation of such crystalline solid substance is not desirable for the purpose of the present invention. If it is necessary to maintain the aqueous solution in a stabilized condition for a long period of time, it is preferred to add oxalic acid to the solution.

To the above-mentioned aqueous solution containing vanadium and phosphorus, an organic solvent such as an alcohol, a ketone or an ether may be added, as the case requires.

According to the present invention, the above-mentioned first and second components are mixed with silica sol as the third component to obtain a slurry, which is then spray-dried to obtain solid particles as the preliminary catalytic composition. The silica sol is preliminarily prepared in the form of a solution containing from 10 to 50% by weight of solid, and the solution is mixed with the first and second components to obtain a uniform slurry. The ratio by dry weight of the first, second and third components is preferably selected within the following range:

first component:second component:third component = 1:0.1–7:0.05–4.

The dry weight of the second component is calculated on the basis of $V_2O_4$ for vanadium and $P_2O_5$ for phosphorus.

If the amounts of the first and second components are too small relative to the third component, the catalytic activities tend to be low, although the strength of the catalyst will thereby be improved. Further, if the amount of the second component relative to the first component is less than the above range, the strength of the catalyst tends to be low.

When the first, second and third components are mixed, it is preferred to use a wet-type mixer such as a ball mill, a rod mill, a stirring mill, a sand grinder, an ultra-homomixer, a disperser or a ultrasonic mill, to make the slurry as uniform as possible and to pulverize the solid particles as fine as possible.

Further, when the three components are mixed, an activity promoting component may be added. As the activity promoting component, there may be mentioned compounds of iron, chromium, aluminum, titanium, cobalt, manganese or nickel, and compounds of an alkaline earth metal such as calcium or magnesium. As such compounds, there may be mentioned inorganic salt such as oxides, hydroxides, chlorides, sulfates, nitrates and carbonates, and organic salts such as acetates or oxalates. The amount of the addition is optionally selected within a range of from 0.0002 to 0.2 mol as the metal atoms per mol of the vanadium atoms.

The slurry thus obtained is then spray-dried to obtain solid particles as the precursory catalytic composition. The above slurry is preferably adjusted so that the oxide concentration in the slurry is usually from 10 to 40%, preferably from 15 to 30% prior to the spray-drying. If the oxide concentration in the slurry is too high, not only the transportation of the slurry becomes difficult but also the solid particles thereby obtained tend to have poor sphericity, whereby the catalytic composition particles finally obtained will have poor flowability. As a spray-drying condition, the temperature of the gas in the drying region is set within a range of from 100° to 350° C., preferably from 100° to 200° C., more preferably from 110° to 150° C. by properly controlling the rates of the air flow and the supply of the slurry. The temperature of the drying gas at the inlet is usually from 200° to 350° C. If the temperature for the spray-drying is too high, the strength of the catalyst composition particles tends to be low. Further, the supply of the solution and the rotational speed of the disk are preferably controlled so that the average particle size of the solid particles after the spray-drying becomes to be within a range of from 30 to 100 μm, more preferably from 40 to 70 μm.

The solid particles thereby obtained are further calcined to obtain an oxidation catalyst composition. The calcination is conducted usually at a temperature of from 400° to 700° C., preferably from 450° to 600° C. As the atmosphere for the calcination, air or air containing an organic substance such as butane or butenes may be used. The calcination may be carried out also in an atmosphere of an inert gas such as argon or nitrogen.

When a precursory oxide is used as the first component for the preparation of the solid particles, the precursory oxide in the solid particles is transformed into a calcined oxide by this calcination.

The catalytic composition obtained in the foregoing manner has superior flowability, strength and catalytic activities and thus suitable for use as a catalyst for a fluidized bed reaction. Further, the catalyst composition of the present invention has a catalytic activity equal to or superior to the single use of the calcined oxide. For instance, the solid particles obtained by the spray-drying may be molded by a conventional manner to obtain a catalyst useful for a fixed bed reaction.

Among the catalyst compositions obtainable by the process of the present invention, the catalytic compositions particularly suitable for use in the fluidized bed reaction have the following specific physical properties. Namely, the catalyst compositions have features such that (i) the content of the crystalline composite oxide is from 15 to 80% by weight, (ii) the atomic ratio of phosphorus to vanadium is from 0.8 to 1.5, (iii) the pore volume of the pores having a pore radius within a range of from 37 to 2000 Å is from 0.03 to 0.3 ml/g, (iv) the pore volume of the pores having a pore radius within a range of from 100 to 350 Å is at least 50% of the pore volume of the pores having a pore radius within a range of from 37 to 2000 Å, (v) the specific surface area is from 0.5 to 20 m$^2$/g, (vi) the average particle size is from 30 to 100 μm and (vii) the shape of the catalyst particles is substantially spherical.

The catalyst compositions having such features are prepared by mixing the above-mentioned first, second and third components in a predetermined ratio to obtain a slurry as uniform as possible and spray-drying the slurry, followed by calcination. The ratio of the first, second and third components must be selected to bring the content of the crystalline complex oxide, the atomic ratio of phosphorus to vanadium and the pore size distribution of the catalyst composition thereby obtained, within the above-mentioned respective ranges. The ratio by dry weight of the first, second and third components is selected usually within the range:

first component:second component:third component = 1:0.1-7:0.05-4, preferably 1:0.3-4:0.5-2. The amount of the first component is selected so that the content of the crystalline composite oxide in the catalyst composition thereby obtained is usually within a range of from 15 to 80% by weight, preferably from 20 to 55% by weight. The first component i.e. the calcined oxide is an active component, and if the amount of the first component is less than 15% by weight, the catalytic activity tends to be poor. On the other hand, if the amount exceeds 80% by weight, the strength of the catalyst tends to be poor. The amount of the second component is selected so that the atomic ratio of phosphorus to vanadium (hereinafter referred to as "a P/V atomic ratio") in the entire catalyst composition is within a range of from 0.8 to 1.5, preferably from 1.1 to 1.3. Namely, the P/V atomic ratio of the first component is usually 1, and the overall P/V atomic ratio will be adjusted by the amounts of phosphorus and vanadium contained in the second component including a certain amount of phosphorous and vanadium which may accompany the crystalline composite oxide during the preparation of the first component. If the P/V atomic ratio is less than 0.8, the selectivity of the catalyst tends to be poor, and if the P/V atomic ratio exceeds 1.5, the catalytic activity of the catalyst tends to be poor. As mentioned above, the second component is an aqueous solution containing vanadium and phosphorus. However, in the final form of the catalyst composition, it forms an amorphous vanadium-phosphorus composite oxide. Accordingly, although the second component itself has a substantially lower activity than the first component, it is highly effective to disperse the first component into the catalyst and particularly it serves to effectively mask fine pores having a pore size of less than 100 Å which are particularly undesirable for a selective oxidation catalyst, whereby it serves to improve the overall catalytic activity.

The catalyst composition obtained in the foregoing manner is porous. The pore volume of the pores having a pore radius within a range of from 37 to 2000 Å is from 0.03 to 0.3 ml/g, and at least 50% of the pore volume is assumed by the pores having a pore radius within a range of from 100 to 350 Å. The pore volume is measured by a mercury penetration method which is commonly used. If the pore volume is too small, the catalytic property tends to be poor. On the other hand, if the pore volume is too great, the mechanical strength of the catalyst tends to be extremely poor. Further, if the proportion of the pores having a pore radius within a range of from 100 to 350 Å, i.e. the pores in a so-called meso pore range, is greater, the catalytic activity is improved. For instance, even when the first component as the active component is present in the catalyst composition only at a level of 35%, the catalyst has an activity as high as that of the calcined oxide itself. Further, a preferred catalyst composition has a substantially spherical shape and its average particle size is from 30 to 100 μm, preferably from 40 to 70 μm and its specific surface area is from 0.5 to 20 m$^2$/g. The specific surface area of the catalyst composition can be controlled mainly by the amount of the second component and the calcination temeprature. If the specific surface area is excessively small, the catalytic activity will be poor. On the other hand, if the specific surface area is too great, selectivity tends to be poor. Accordingly it is preferred that the specific surface area be adjusted within the above-mentioned range.

The oxidation catalyst composition obtained by the process of the present invention has superior flowability, strength and catalytic activity and is suitable for use as a catalyst for the production of maleic anhydride by the oxidation of a hydrocarbon having at least four carbon atoms, particularly, n-butane.

The present invention will be described in further detail with reference to Examples. However, it should be unerstood that the present invention is by no means restricted to such Examples.

EXAMPLE 1

(A) Preparation of the first component (a calcined oxide)

Into a 100 l tank with glass lining and equipped with a stirrer, 40 l of deionized water was introduced, and 9.22 kg of phosphoric acid (85%, special grade reagent), 1.30 kg of hydrazine dihydrochloride and 550 g of hydrazine monohydrochloride were added and dissolved. The solution was heated to 75° C. and 7.28 kg of vanadium pentoxide was gradually added under stirring. After the addition of the total amount, the solution was boiled for one hour to complete the reduction. The solution was concentrated by a rotary evaporator under reduced pressure until the amount of the solution became about ½. The concentrated solution was put in six evaporation vessels and evaporated at 170° C. to dryness. After confirming that the constant weight was reached, the dried product was roughly pulverized and the solid was boiled and washed with water, followed by filtration to completely remove the remaining hydrochloric acid. After washing with water, the solid was again dried at a temperature of 170° C. and finely pulverized by a hammer mill to obtain a precursory oxide having a P/V atomic ratio of 1.

A portion of this precursory oxide was calcined at 500° C. for 2 hours in a nitrogen stream and then calcined at the same temperature for 1 hour under an air stream. The first component thereby obtained was confirmed by the X-ray diffraction measurement to show the diffraction peaks as identified in Table B.

(B) Preparation of the second component

Into 1000 ml of deionized water, 1865 g of phosphoric acid (85%, special grade reagent) and 1500 g of oxalic acid were dissolved, and the solution was heated to 80° C. Then, 1082 g of vanadium pentoxide was gradually added and dissolved therein. The P/V atomic ratio in the solution was 1.36 and the solution was a slightly viscous blue colored uniform solution. The solution was concentrated to some extent to bring the weight of the solution to 4.75 kg and to adjust the oxide concentration to 45.0% by weight as calculated as ($V_2O_4 + P_2O_5$).

(C) Preparation of a catalyst composition

The first component obtained in Example 1 (A), the second component obtained in Example 1 (B) and a silica sol slurry ($SiO_2$ concentration: 20% by weight) as the third component were mixed to obtain a slurry to be spray-dried. The mixing ratio was as follows:
first component 1.467 kg
second component 1.087 kg
third component 2.446 kg The mixture was thoroughly mixed for 40 minutes by a homogenizer to obtain a uniform slurry to be spray-dried. The slurry was sprayed by a high speed rotary disk rotating at a speed of 15,000 rpm and contacted and dried with a high temperature drying air (inlet temperature: 278° C.). The supply rate of the slurry was 16 l/hr. The solid particles thereby obtained was calcined at 500° C. for 2 hours in a nitrogen stream to obtain a catalyst composition. The solid particles were sieved to obtain particles having a particle size within a range of from 25 to 88 μm and the particles thereby obtained were subjected to the activity test and the strength test. The strength was determined in such a manner that under the fluidized condition, the catalyst composition particles were driven at a high speed to collide against a metal plate and the destruction loss (%) within 2 hours was measured and taken as an index of the mechanical strength. The greater the strength of the catalyst, the smaller the value of the destruction loss.

EXAMPLE 2

(C) Preparation of a catalyst composition

A catalyst composition was obtained by conducting the spray-drying, the calcination and the sieving in the same manner as in Example 1 except that instead of the first component (the calcined oxide) in Example 1 (C), 1.639 kg of the precursory oxide having a P/V atomic ratio of 1 obtained in Example 1 (A) was used without being calcined.

EXAMPLES 1 AND 2

(D) Reaction Example

With use of an air-gas mixture containing 4 molar % of n-butane and 20 ml of the catalyst, an activity test was conducted at GHSV 500 by means of a small fluidized bed reactor. The results thereby obtained are shown in Table 1. It is evident that when the precursory oxide was preliminarily calcined, the strength and catalytic activity of the catalyst were improved.

TABLE 1

| Catalyst | Strength (%) | Optimum temperature (°C.) | Conversion of n-butane (%) | Yield of maleic anhydride (%) |
|---|---|---|---|---|
| Example 1 | 10 | 440 | 78.0 | 37.5 |
| Example 2 | 21 | 440 | 78.0 | 34.1 |

EXAMPLE 3

(A) Preparation of the first component (a precursory oxide; A-1)

Into 40 l of deionized water, 9.22 kg of phosphoric acid (85%, special grade reagent), 1.30 kg of hydrazine dihydrochloride and 550 g of hydrazine monohydrochloride were dissolved, and the solution was heated. After the temperature reached 75° C., 7.28 kg of vanadium pentoxide was gradually added under stirring, and after the addition of the total amount, the solution was boiled for 1 hour to complete the reduction. This solution was concentrated by a rotary evaporator under reduced pressure until the amount of the solution became about ½. The concentrated solution was placed in an evaporation vessel and evaporated at 170° C. to dryness. After confirming that the constant weight was reached, the dried product was roughly pulverized and the solid thereby obtained was boiled and washed with water to completely remove the remaining hydrochloric acid. After filtration and washing with water, the solid was dried again at 170° C. in a dryer and then finely pulverized in a hammer mill to obtain the first component (A-1) having a P/V atomic ratio of 1. The average particle size was 6.5 μm. The X-ray diffraction spectrum of this first component was the same as shown in Table A.

(B) Preparation of the second component (B-1)

In 500 ml of deionized water, 1635 g of phosphoric acid (85% solution) and 1500 g of oxalic acid were dissolved, and the solution was heated to 80° C. Then, 1082 g of vanadium pentoxide was gradually added and dissolved therein. The P/V atomic ratio of the solution was 1.2, and the solution was a slightly viscous blue-colored uniform solution. The solution was concentrated to some extent to bring the oxide concentration to 45.0% by weight as calculated as ($V_2O_4 + P_2O_5$) and to obtain the second component (B-1). The molar ratio of the remaining oxalic acid to the vanadium element was 0.5 since 1 mol of oxalic acid per mol of vanadium pentoxide was used in the reduction reaction.

(C) Preparation of a catalyst composition (Catalyst No. 1)

The first component obtained in Example 3 (A), the second component obtained in Example 3 (B) and silica sol as the third component were mixed in the ratio as shown in Table 3. They were thoroughly mixed by a homogenizer and then the mixture was spray-dried to obtain solid particles. The solid particles thereby obtained were calcined at 500° C. for 2 hours in a nitrogen stream to obtain a catalyst composition (Catalyst No. 1). The catalyst composition was sieved to obtain particles having a particle size within a range of from 25 to 88 μm and the particles were subjected to the activity test and the strength test. The strength of the catalyst was determined in such a manner that in a fluidized condition, the catalyst particles were driven to collide against a metal plate and the destruction loss (%) within 2 hours was measured and taken as an index of the mechanical strength. The greater the strength of the catalyst, the smaller the value of the destruction loss. The results thereby obtained are shown in Table 3.

EXAMPLE 4

(B) Preparation of the second component (B-2)

A blue-colored uniform solution B-2 having a calculated oxide concentration of 45.0% by weight was obtained in the same manner as in Example 3 (B) except that in Example 3 (B), the amount of oxalic acid was changed to 1125 g. The P/V atomic ratio of this solution was 1.2. The molar ratio of the remaining oxalic acid to the vanadium element was 0.25.

(C) Preparation of a catalyst composition (Catalyst No. 2)

A catalyst composition (Catalyst No. 2) was prepared in the same manner as in Example 3 (C) except that in Example 3 (C), the second component (B-2) obtained in Example 4 (B) was used instead of the second component (B-1) of Example 3 (B). The results thereby obtained are shown in Table 3.

EXAMPLE 5

(A) Preparation of the first component (precursory oxide A-2)

In 1.9 l of deionized water, 691.8 g of phosphoric acid, 104.7 g of hydrazine dihydrochloride and 30.0 g of hydrazine monohydrochloride were dissolved and heated. After the temperature reached 75° C., 518.4 g of vanadium pentoxide was gradually added under stirring, and after the addition of the total amount, the mixture was boiled for 1 hour to complete the reduction. After cooling, a solution prepared by dissolving 81.0 g of ferric chloride (FeCl$_3$.6H$_2$O) in 100 g of water, was added thereto. This solution was concentrated until the amount of the solution became about ⅔ and then evaporated at a temperature of 170° C. in a evaporating vessel to dryness. After confirming that the constant weight was reached, the dried product was treated in the same manner as in Example 1 to obtain the first component (A-2) having a P/V/Fe atomic ratio of 1/0.9./0.1. The X-ray diffraction peaks of this product were within the range of ±0.2° of the positions of the respective peaks shown in Table A.

(C) Preparation of a catalyst composition (Catalyst No. 3)

A catalyst composition (Catalyst No. 3) was prepared in the same manner as in Example 3 (C) except that in Example 3 (C), the first component (A-2) obtained in Example 5 (A) was used instead of the first component (A-1) of Example 3 (A). The results thereby obtained are shown in Table 3.

EXAMPLES 6 TO 10

(A) Preparation of the first components (precursory oxides A-3 to A-7)

The first components A-3 to A-7 having the elemental ratios are shown in the following Table 2 were prepared in the same manner as in Example 5 (A) except that instead of the ferric chloride used as the substitution component in Example 5 (A), chromium chloride, aluminum chloride, titanium oxalate, cobalt chloride and magnesium chloride were respectively used. As the atomic ratios were modified, the amounts of the starting materials in Example 5 (A) were adjusted accordingly. In Table 2, A-1 and A-2 are also presented.

TABLE 2

| No. | Substitution component (Me) | Atomic ratio | | |
|---|---|---|---|---|
| | | V | Me | P |
| A-1 | — | 1 | 0 | 1 |
| A-2 | Fe | 0.9 | 0.1 | 1 |
| A-3 | Cr | 0.95 | 0.05 | 1 |
| A-4 | Al | 0.9 | 0.1 | 1 |
| A-5 | Ti | 0.9 | 0.1 | 1 |
| A-6 | Ti/Co | 0.94 | 0.04/0.02 | 1 |
| A-7 | Mg | 0.95 | 0.05 | 1 |

(C) Preparation of catalyst compositions (Catalysts Nos. 4 to 8)

Catalyst compositions (Catalysts Nos. 4 to 8) were prepared in the same manner as in Example 3 (C) except that in Example 3 (C), the first components (A-3 to A-7) obtained in Examples 6 (A) to 10 (A) were used instead of the first component (A-1) of Example 3 (A). The results thereby obtained are shown in Table 3.

TABLE 3

| | | Preparation of Catalysts for a Fluidized Bed Reaction | | | | | | |
|---|---|---|---|---|---|---|---|---|
| Example No. | Catalyst No. | First Component (kg) | Second Component (kg) | Third Component (%)* (kg)** | Supply rate of the solution (l/hr) | Temp. of gas at the inlet of the spray-drier (°C.) | Rotational speed of the disk (rpm) | Strength (%) |
| 3 | 1 | A-1 1.12 | B-1 1.73 | 20 2.22 | 11.0 | 300 | 15,000 | 13 |
| 4 | 2 | A-1 1.59 | B-2 1.05 | 20 2.36 | 15.9 | 278 | 15,000 | 21 |
| 5 | 3 | A-2 1.12 | B-1 1.73 | 20 2.22 | 10.6 | 300 | 12,000 | 12 |
| 6 | 4 | A-3 1.12 | B-1 1.73 | 20 2.22 | 10.7 | 300 | 12,000 | 16 |
| 7 | 5 | A-4 1.12 | B-1 1.73 | 20 2.22 | 10.6 | 300 | 12,000 | 10 |
| 8 | 6 | A-5 1.12 | B-1 1.73 | 20 2.22 | 10.5 | 300 | 12,000 | 15 |

TABLE 3-continued

| | | | | Preparation of Catalysts for a Fluidized Bed Reaction | | | | |
|---|---|---|---|---|---|---|---|---|
| Example No. | Catalyst No. | First Component (kg) | Second Component (kg) | Third Component (%)* (kg)** | Supply rate of the solution (l/hr) | Temp. of gas at the inlet of the spray-drier (°C.) | Rotational speed of the disk (rpm) | Strength (%) |
| 9 | 7 | A-6 1.12 | B-1 1.73 | 20 2.22 | 10.7 | 300 | 12,000 | 9 |
| 10 | 8 | A-7 1.12 | B-1 1.73 | 20 2.22 | 10.5 | 300 | 12,000 | 10 |

*Silica sol, $SiO_2$ concentration
**Weight of the silica sol slurry

EXAMPLES 3 TO 10

(D) Reaction Example 1

With respect to the catalyst compositions obtained in Examples 3 (C) to 10 (C), 20 ml of each catalyst was used and the reaction was conducted by passing an air-gas mixture containing 4 molar % of n-butane therethrough at a flow rate of GHSV 500. The product was absorbed in water, and the yield was determined by potentiometric titration and analysis of the exhaust gas composition. The results thereby obtained are shown in Table 4.

TABLE 4

| Example No. | Catalyst No. | Optimum reaction temperature (°C.) | Conversion of n-butane (%) | Yield of maleic anhydride (%) |
|---|---|---|---|---|
| 3 | 1 | 426 | 81.2 | 38.8 |
| 4 | 2 | 440 | 78.0 | 34.1 |
| 5 | 3 | 420 | 76.5 | 37.0 |
| 6 | 4 | 418 | 85.4 | 41.5 |
| 7 | 5 | 432 | 75.4 | 36.9 |
| 8 | 6 | 412 | 78.8 | 37.0 |
| 9 | 7 | 405 | 79.5 | 39.0 |
| 10 | 8 | 433 | 76.2 | 38.1 |

(D) Reaction Example 2

With use of the catalysts obtained in Examples 3 and 5, the influence of the reaction conditions was investigated.

The reaction was conducted in the same manner as in the above (D) Reaction Example 1 except that only the n-butane concentration was varied while maintaining the flow rate to be constant at GHSV=500, and the performance of the reaction was investigated. The results are shown in Table 5.

TABLE 5

| Example No. | Catalyst No. | Concentration of n-butane (mol ratio) | Optimum reaction temp. (°C.) | Conversion of n-butane (%) | Yield of maleic anhydride (%) |
|---|---|---|---|---|---|
| 3 | 1 | 4.1 | 430 | 77.0 | 36.5 |
| | | 3.0 | 420 | 82.0 | 45.6 |
| | | 1.6 | 410 | 86.2 | 47.2 |
| 5 | 3 | 4.0 | 420 | 76.5 | 37.0 |
| | | 2.9 | 410 | 80.0 | 43.5 |
| | | 1.6 | 390 | 84.5 | 49.9 |

EXAMPLE 11

(B) Preparation of the second component (B-3)

A slurry was obtained by mixing 1.33 kg of $V_2O_5$, 0.844 kg of 85% phosphoric acid, 0.660 kg of phosphorous acid (purity: 97.6%) and 4.5 l of water. The slurry was boiled and refluxed for 10 hours while stirring and supplying a small amount of nitrogen. $V_2O_5$ was completely dissolved to give a blue-colored uniform solution. The solution was diluted to 10 l to obtain a solution of the second component (B-3). The calculated oxide concentration of this solution was about 18.5% by weight. The P/V atomic ratio of this solution was 1.05. The solution was stored in a cool dark place. When in use, an optional amount of phosphoric acid was added to adjust the phosphoric acid content.

(C) Preparation of a catalyst composition (Catalyst No. 9)

A uniformly gelled slurry was obtained by mixing 1.12 kg of the first component obtained in Example 3 (A), 3.38 l of the aqueous solution obtained as the second component in Example 11 (B), 2.22 kg of a 20% silica sol solution as the third component and 77 kg of 85% phosphoric acid and then stirring the mixture for 60 minutes by a homogenizer. The oxide concentration was 30% by weight. This slurry was spray-dried to obtain solid particles. The solid particles were calcined at 500° C. for 2 hours in a nitrogen stream to obtain a catalyst composition (Catalyst No. 9). The catalyst composition was sieved to obtain particles having a particle size within a range of from 25 to 88 μm and the particles were used for a reaction.

EXAMPLE 12

(C) Preparation of a catalyst composition (Catalyst No. 10)

A catalyst composition (Catalyst No. 10) was prepared in the same manner as in Example 11 (C) except that the amount of the phosphoric acid was 130 g.

EXAMPLES 11 AND 12

(D) Reaction Example

With respect to the catalyst compositions obtained in Examples 11 and 12, 20 ml of each catalyst was used and a fluidized bed reaction was conducted by passing an air-gas mixture containing 4 molar % of n-butane therethrough at a flow rate of GHSV 500. In the same manner as in Examples 3 to 10 (D) Reaction Example 1, the product was absorbed in water and the yield was determined by potentiometric titration and analysis of the exhaust gas composition. The results thereby obtained are shown in Table 6.

TABLE 6

| Example No. | Catalyst No. | Optimum reaction temperature (°C.) | Conversion of n-butane (%) | Yield of maleic anhydride (%) |
|---|---|---|---|---|
| 11 | 9 | 463 | 85.7 | 39.4 |

TABLE 6-continued

| Example No. | Catalyst No. | Optimum reaction temperature (°C.) | Conversion of n-butane (%) | Yield of maleic anhydride (%) |
|---|---|---|---|---|
| 12 | 10 | 476 | 84.3 | 40.2 |

EXAMPLE 13

(A) Preparation of the first component (Precursory oxide)

In a 100 l container with glass lining and provided with a jacket, 24.6 l of water and 14.156 kg of 85% phosphoric acid were mixed and 1.73 kg of a 85% hydrazine hydrate solution was added and stirred. Then, 10.635 kg of vanadium pentoxide was added while paying a careful attention to the generation of bubbles, whereby a uniform blue solution was obtained. Thereafter, the temperature was raised and after confirming the termination of the generation of bubbles, the temperature of the solution was raised to 120° C. The time required for the temperature rise was about 1 hour. The heating was continued for further 12 hours at the same temperature to complete hydrothermal treatment. A small amount of the slurry was filtered and the light blue precipitates were subjected to an X-ray diffraction measurement, whereby it was confirmed that the precipitates gave the X-ray diffraction peaks as shown in Table A. From the results of the elemental analysis, the composition of the solid was found to be generally represented by the formula $(V_2O_4)(P_2O_5)(2H_2O)$. The slurry concentration as represented by this formula corresponds to 40% by weight. The aqueous slurry thereby obtained was filtered by a centrifugal filtration apparatus to obtain about 27 kg of the filtrate and 23.1 kg of a wet cake. The cake was dried in a hot air drier at 170° C. until the constant weight was reached, whereby the first component was obtained.

(B) Preparation of the second component

The filtrate obtained by the filtration of the above-mentioned aqueous slurry was light blue thus indicating the dissolution of tetravalent vanadyl ions. To this filtrate, 9.25 kg of 85% phosphoric acid and 8.95 kg of oxalic acid were added and dissolved under heating, and then 6.46 kg of vanadium pentoxide was gradually added and dissolved, whereby the second component was obtained.

(C) Preparation of a catalyst composition

By means of a homogenizer, 5.0 kg of the dried cake obtained as the first component in the above (A), 13.7 kg of the second component obtained in the above (B) and 5.0 kg of 40% silica sol solution as the third component were thoroughly mixed for 40 minutes. The slurry thereby obtained was highly viscous and at least partially gelled. The total concentration of the oxides $(V_2O_4+P_2O_5)$ in the solution portion of the slurry and the crystalline oxide was about 40% by weight. The ratio of the crystalline oxide, the oxide in the solution portion and silica sol in the slurry was 45/35/20. The slurry thereby obtained was spray dried by means of a spray drier. The slurry was sprayed by a rotary disk rotating at a rotational speed of 15,000 rpm and contacted and dried with heated air. The temperature of the drying air was 270° C. at the inlet and the gas temperature at the outlet of the spray drier was 138° C.

The solid particles thereby obtained (P/V atomic ratio: 1.088) was calcined in a fluidized condition at 500° C. for 2 hours in a nitrogen stream and thereby activated to obtain a catalyst composition. The catalyst composition was classified and used for a reaction.

(D) Reaction Example 1

The catalyst composition obtained in the above (C) was classified by sieving to obtain particles having a particle size within a range of from 25 to 88 μm. The average particle size of the classified particles was 56 μm. 50 ml of the particles were filled in a small fluidized bed reactor. Air-gas mixtures having various concentrations of n-butane were introduced into the reactor and reacted at a flow rate of GHSV 500. The products thereby obtained were respectively absorbed in water and quantitatively analyzed by potentiometric titration and gas chromatography analysis of the exhaust gas. The results of the reactions are shown in Table 7.

TABLE 7

| Concentration of n-butane (molar %) | Optimum temperature (°C.) | Conversion of n-butane (%) | Yield of maleic anhydride (%) |
|---|---|---|---|
| 4.05 | 440 | 77.0 | 37.5 |
| 2.95 | 420 | 82.0 | 45.6 |
| 1.58 | 410 | 86.2 | 47.2 |

EXAMPLE 14

(A) Preparation of the first component (Precursory oxide) and the second component In a 10 l beaker, 622.55 g of 85% phosphoric acid, 73.6 g of a 85% hydrazine hydrate aqueous solution and 2550 g of deionized water were mixed, and then 454.75 g of vanadium pentoxide was added and stirred. With the generation of bubbles, the temperature of the solution rised to about 60° C. When the generation of bubbles was substantially terminated, the solution was heated to the boiling point to complete the reaction.

This solution was boiled and concentrated until the weight of the solution became 2500 g. Then, the concentrated solution was transferred to a 2.5 l autoclave and heated to 130° C., and the hydrothermal treatment was conducted for 5 hours. The resulting viscous slurry was cooled and transferred with a small amount of water to a 10 l beaker. Then, 384.46 g of 85% phosphoric acid, 382.80 g of oxalic acid, 600 ml of water and 276.16 g of vanadium pentoxide were added, and the temperature was slowly raised under stirring. With the generation of bubbles, the reduction proceeded and after the entire mixture turned into a blue-colored slurry, the slurry was further boiled to complete the reduction.

The slurry was concentrated until the weight of the entire slurry became 3200 g. The total concentration of the oxides $(V_2O_4+P_2O_5)$ in the solution portion of the slurry and the crystalline oxide in the slurry thereby obtained was 40% by weight. The weight ratio of the crystalline oxide and the oxides in the solution portion was about 58:42. A small amount of solid was filtered from the slurry and subjected to an X-ray diffraction measurement, whereby the X-ray diffraction peaks were found to be identical with the X-ray diffraction peaks shown in Table A. These are the same as the X-ray diffraction peaks of the crystals in the slurry obtained by the hydrothermal treatment, whereby it was found that no change in the crystal structure took place during the secondary dissolving step of the vanadium pentoxide.

(C) Preparation of a catalyst composition

To the aqueous slurry of the first and second components obtained in the above (A), 1800 g of 30% silica sol was added and the mixture was thoroughly mixed by a homogenizer to obtain a viscous slurry to be spray dried. The slurry was spray-dried under the same conditions as in Example 13 (C). The solid particles thereby obtained was calcined at 350° C. for 1 hour in an air stream and then at 500° C. for 2 hours in a nitrogen stream and thereby activated to obtain a catalyst composition. The catalyst composition was classified and used for a reaction. The $SiO_2$ content in the catalyst as calculated as oxides was 30% by weight.

EXAMPLE 15

(A) Preparation of the first component (Calcined oxide)

In the same manner as in Example 13 (A), a slurry containing the crystalline oxide was obtained and filtered by a centrifugal filtration apparatus, and the cake thereby obtained was dried. The cake was pulverized into small aggregates and calcined for 2 hours in a nitrogen stream in a calcination tube. The X-ray diffraction peaks of the calcined product were the same as those shown in Table B. About 18.0 kg of the small aggregates thereby obtained were finely pulverized by a hammer mill to obtain the first component.

(B) Preparation of the second component

To 3500 g of the filtrate obtained by the filtration of the aqueous slurry in Example 15 (A), 1180 g of 85% phosphoric acid and 800 g of oxalic acid were added and dissolved under heating, and then 576.6 g of vanadium pentoxide was gradually added and dissolved to obtain the second component.

(C) Preparation of a catalyst composition

To the second component obtained in Example 15 (B), 1785 g of a 40% silica sol solution was added and 1000 g of the finely pulverized first component obtained in Example 15 (A) was added. The mixture was thoroughly mixed by a homogenizer to obtain a slurry to be spray-dried. The slurry was spray-dried under the same condition as in Example 13 (C). The solid particles thereby obtained were calcined at 350° C. for 1 hour in an air stream and then at 500° C. for 2 hours in a nitrogen stream and thereby activated to obtain a catalyst composition. The catalyst composition was classified and used for a reaction. The $SiO_2$ content in the catalyst as calculated as oxides was 25% by weight.

EXAMPLES 14 AND 15

(D) Reaction Example

The catalysts obtained in Examples 14 (C) and 15 (C) were classified in the same manner as in the Reaction Example 13 (D) and subjected to the activity test under the same conditions. The results thereby obtained are shown in Table 8.

TABLE 8

| Example No. | Concentration of n-butene (molar %) | Optimum temperature (°C.) | Conversion of n-butane (%) | Yield of maleic anhydride (%) |
|---|---|---|---|---|
| 14 | 4.0 | 420 | 76.5 | 37.0 |

TABLE 8-continued

| Example No. | Concentration of n-butene (molar %) | Optimum temperature (°C.) | Conversion of n-butane (%) | Yield of maleic anhydride (%) |
|---|---|---|---|---|
| 15 | 4.0 | 460 | 76.7 | 39.7 |

EXAMPLE 16

(A) Preparation of the first component (Calcined oxide)

Into a 100 l pressure container with glass lining and provided with a jacket, 38.0 kg of deionized water, 21.83 kg of 85% phosphoric acid and 2.85 kg of a 80% hydrazine hydrate solution were fed and stirred to obtain a uniform solution. While paying a careful attention to the generation of bubbles, 16.40 kg of vanadium pentoxide was gradually added thereto and dissolved. During this operation, a cooling medium was circulated in the jacket to maintain the temperature of the solution at a level of from 60° to 80° C. After the dissolution was completed and the generation of bubbles ceased, 1.0 kg of seed crystals of the precursory oxide was added and the solution was heated under a closed condition by circulating a high temperature medium preliminarily heated to a temperature of 160° C. in the jacket. The temperature was raised to 140° C. in 1.5 hours. The heating and stirring were continued for 10 hours. During the period, the inner pressure of the container was constant at a level of about 2.4 kg/cm²G. After cooling the slurry to 90° C., 10.3 kg of deionized water was added and the content was withdrawn and left for cooling. A small amount of this slurry was filtered, and the light blue solid thereby obtained was subjected to an X-ray diffraction measurement, whereby the X-ray diffraction peaks were found to be identical with the X-ray diffraction peaks shown in Table A. After being uniformly mixed by a stirrer, the slurry was spray-dried by a spray drier having a high speed rotary disk to obtain a fine powder precursory oxide. The spray-drying was conducted under such condition that the temperature of the gas was from 330° to 370° C. at the inlet and 160° C. at the outlet. The P/V atomic ratio of this powder was 1.05.

The precursory oxide thus obtained was calcined in a small rotary kiln at a temperature of 520° C. for a retention time of 15 minutes in a nitrogen gas stream. The X-ray diffraction spectrum of the calcined oxide was identical with that shown in Table B. Further, the ratio of the pentavalent vanadium in the total vanadium in the calcined oxide was 0%.

(B) Preparation of the second component

In 50 kg of deionized water, 6.929 kg of 85% phosphoric acid and 4.789 kg of oxalic acid ($H_2C_2O_4.2H_2O$) were added and dissolved under stirring and heating to 80° C. While paying a careful attention to the generation of bubbles, 4.319 kg of vanadium pentoxide was added thereto and dissolved. The solution was cooled and water was added to bring the total weight to 67.1 kg, whereby the second component was obtained.

(C) Preparation of a catalyst composition

To 20.0 kg of the second component obtained in Example 16 (B), 3.82 kg of a 40% silica sol solution as the third component and 2.14 kg of the first component (the calcined oxide) obtained in Example 16 (A) were added to obtain a slurry. This slurry was subjected to a continuous wet-type mill to obtain a sufficiently uniform slurry and then spray-dried by a spray drier provided with a high speed rotary disk. The spray-drying was conducted under such condition that the temperature of the gas was from 200° to 210° C. at the inlet and from 120° to 130° C. at the outlet. The average particle size of the solid particles thereby obtained was within a range of from 58 to 62 μm. The spray-dried product was calcined in a fluidized calcination furnace at a temperature of 350° C. for 1 hour in an air stream and further calcined at 500° C. for 2 hours in a nitrogen gas stream and thereby activated to obtain a catalyst composition (Catalyst No. 11). The catalyst composition was sieved to obtain particles having a particle size within a range of from 44 to 116 μm and the particle were used for a reaction.

EXAMPLE 17

(A) Preparation of the first component (Calcined oxide)

The precursory oxide obtained in Example 16 (A) was calcined in a small rotary kiln at a temperature of 520° C. for a retention time of 15 minutes in a nitrogen gas stream and then further calcined in the same rotary kiln at a temperature of 580° C. for a retention time of 15 minutes under an air stream. The X-ray diffraction peaks of the calcined product were identical with those shown in Table B and the ratio of the pentavalent vanadium in the total vanadium was 21.7%.

EXAMPLE 18

(A) Preparation of the first component (Calcined oxide)

The precursory oxide obtained in Example 16 (A) was calcined in a small rotary kiln at a temperature of 500° C. for a retention time of 15 minutes in a stream of air diluted with nitrogen (oxygen concentration: 2%). The X-ray diffraction peaks of this product were identical with those shown in Table B and the ratio of the pentavalent vanadium in the total vanadium was 16.3%.

EXAMPLE 19

(A) Preparation of the first component (Calcined oxide)

The precursory oxide obtained in Example 16 (A) was put in an amount of 1 kg in each of porcelain calcination dishes having a capacity of 2 l. The dishes were piled in a spaced manner in a muffle furnace having inner volume of 500 l. The interior of the furnace was flushed with a nitrogen gas and then heated and the precursory oxide was calcined at 550° C. for 2 hours. Then, air was gradually introduced into the furnace and heated at a temperature of 550° C. for 1 hour and then cooled. The X-ray diffraction peaks of the calcined product were identical with those shown in Table B and the ratio of the pentavalent vanadium in the total vanadium was 23.4%.

EXAMPLE 20

(A) Preparation of the first component (Calcined oxide)

A calcined oxide was prepared in the same manner as in Example 19 (A) except that in Example 19 (A), the calcination temperature was changed to 600° C. The X-ray diffraction peaks of the calcined oxide thereby obtained were subtantially the same as those shown in Table B. However, a broad weak peak was observed at $2\theta = 21.4°$. The ratio of the pentavalent vanadium in the total vanadium was 35.2%.

EXAMPLES 17 TO 20

(C) Preparation of catalyst compositions (Catalysts Nos. 12 to 15)

Catalyst compositions (Catalysts Nos. 12 to 15) were obtained in the same manner as in Example 16 (C) except that in Example 16 (C), the first components obtained in Examples 17 (A) to 20 (A) were respectively used instead of the first component of Example 16 (A).

EXAMPLES 16 TO 20

(D) Reaction Example

The catalyst compositions (Catalysts Nos. 1 to 5) obtained in Examples 16 (C) to 20 (C) were respectively introduced into fluidized bed reactors made of heat resistant glass, and air containing 3% by volume of n-butane was introduced thereinto at a flow rate of GHSV 500 to carry out the production of maleic anhydride. The products were absorbed in water. The reaction products were analyzed by potentiometric titration and gas chromatography of the exhaust gas. The results thereby obtained are shown in Table 9.

TABLE 9

| Example No. | Catalyst No. | Ratio of the pentavalent vanadium in the first component (%) | Optimum reaction temperature (°C.) | Conversion of n-butane (%) | Yield of maleic anhydride (%) |
|---|---|---|---|---|---|
| 16 | 1 | 0 | 460 | 70.5 | 34.7 |
| 17 | 2 | 21.7 | 420 | 94.0 | 50.9 |
| 18 | 3 | 16.3 | 431 | 89.1 | 49.2 |
| 19 | 4 | 23.4 | 420 | 83.5 | 50.6 |
| 20 | 5 | 35.2 | 433 | 90.4 | 46.3 |

EXAMPLE 21

(A) Preparation of the first component (Precursory oxide)

Into a 100 l pressure container with glass lining and provided with a jacket, 38.0 kg of deionized water, 21.83 kg of 85% phosphoric acid and 2.85 kg of a 80% hydrazine hydrate solution were fed, and then while paying a careful attention to the generation of the bubbles, 16.40 kg of vanadium pentoxide powder was gradually added and dissolved under stirring. During this period, a cooling medium was circulated in the jacket to control the temperature rise due to the exothermal reaction and to maintain the temperature of the solution at a level of from 60° to 80° C. The addition of vanadium pentoxide was completed in about 4 hours, whereby a blue-colored vanadyl phosphate solution was obtained. To this solution, 1.0 kg of seed crystals were added and the solution was heated by circulating a heating medium heated to 160° C. in the jacket. The temperature of the solution was raised to 140° C. in 2 hours and hydrothermal treatment was continued for 10 hours at the temperature. During this period, the pressure was about 2.4 kg/cm$^2$G. After cooling the reaction mixture to 90° C., 10.3 kg of deionized water was added to adjust the solid concentration in the slurry to about 35% and then the slurry was withdrawn to obtain the first component. This solid was subjected to an X-ray diffraction measurement, whereby it showed the characteristic X-ray diffraction peaks as identified in Table A and thus it was confirmed to be a pure precursory oxide. Further, the particle size distribution of the solid in the slurry was investigated by a Coulter counter method, whereby the average particle size was found to be 0.7 μm. The P/V atomic ratio based on the feed materials of this oxide slurry was 1.05.

(B) Preparation of the second component

In 50 kg of deionized water, 6.929 kg of 85% phosphoric acid and 4.789 kg of oxalic acid ($H_2C_2O_4.2H_2O$) were added and dissolved under stirring and heating to 80° C. While paying a careful attention to the generation of bubbles, 4.319 kg of vanadium pentoxide was gradually added and dissolved and then the solution was cooled. Water was added to bring the total amount of the solution to 67.1 kg. The P/V atomic ratio of this solution was 1.266 and the solution contained 0.8 mol of oxalic acid per gram atom of vanadium. This solution was stable and no precipitation of solid took place even when stored at room temperature for one month.

(C) Preparation of a catalyst composition

To 20 kg of the vanadyl phosphate solution obtained as the second component in the above (B), 6.80 kg of the precursory oxide slurry obtained as the first component in the above (A) was added under stirring. Then, 3.82 kg of a 40% silica sol solution as the third component was added under stirring. This slurry was treated by a continuous wet-type mill to obtain a suffficiently uniform slurry. The slurry was spray-dried by means of a spray drier provided with a high speed rotary disk. The solid concentration of the slurry was 20% and the temperature of the drying gas was 250° C. at the inlet and 140° C. at the outlet. The solid particles thereby obtained had an average particle size of 58 μm and they had satisfactory sphericity and strength.

The solid particles thus obtained were introduced into a fluidized bed and calcined at 350° C. for 1 hour in an air atmosphere and further calcined at 500° C. for 2 hours in a nitrogen atmosphere, whereby a catalyst composition was obtained. The catalyst composition obtained by the calcination was subjected to an X-ray diffraction measurement, whereby it showed the diffraction peaks as identified in Table B and thus it was confirmed that the precursory oxide obtained by the hydrothermal treatment was converted to a calcined oxide of the formula $(VO)_2P_2O_7$ during the preparation of the catalyst composition. Further, the intensity of the diffraction peaks was substantially the same as the strength expected from the amount of the precursory oxide used in the preparation of the catalyst composition. Accordingly, it is considered that during the process for the preparation of the catalyst composition, no destruction of the crystalline oxide took place and no conversion of the vanadium-phosphorus oxide in the vanadyl phosphate solution used as a binder to a crystalline oxide took place.

(D) Reaction Example

The catalyst composition obtained in Example 21 (C) was sieved to obtain particles having a particle size within a range of from 44 to 116 μm and the particles were subjected to an activity test by means of a small fluidized bed reactor. Namely, 20 ml of the catalyst composition was introduced into a reaction tube having an inner diameter of 17 mm and an air-gas mixture containing 3% by volume of n-butane was introduced into the reactor at a flow rate of GHSV 500 to carry out the reaction. The product was absorbed in water. The performance of the reaction was determined by potentiometric titration of the aqueous solution thereby obtained and gas chromatography of the exhaust gas. As a result, it was found that the optimum reaction temperature was 445° C., the conversion of butane at that time was 82.0% and the yield of maleic anhydride was 44.0%.

EXAMPLE 22

(A) Preparation of the first component (Precursory oxide)

Into a 100 l pressure container with glass lining and provided with a jacket, 38.0 kg of deionized water, 21.83 kg of 85% phosphoric acid and 2.85 kg of a 80% hydrazine hydrate solution were fed, and while paying a careful attention to the generation of bubbles, 16.40 kg of vanadium pentoxide powder was gradually added under stirring. During this period, a cooling medium was circulated in the jacket to control the temperature rise due to the exothermal reaction and to maintain the temperature of the solution at a level of from 60° to 80° C. The addition of vanadium pentoxide was completed in about 4 hours, whereby a blue-colored vanadyl phosphate solution was obtained. To this solution, 1.0 kg of seed crystals were added and the solution was heated by circulating a high temperature medium heated to 160° C. in the jacket. The temperature of the solution was raised to 140° C. in 2 hours, and the hydrothermal treatment was continued for 10 hours at the same temperature. During this period, the pressure was about 2.4 kg/cm$^2$G. After cooling the reaction mixture to 90° C., 10.3 kg of deionized water was added to adjust the solid concentration in the slurry to about 35% and then the slurry was withdrawn. The solid thereby obtained was subjected to an X-ray diffraction measurement, whereby it was found that the solid showed the characteristic X-ray diffraction peaks as identified in Table A and it was confirmed that the solid was a pure precursory oxide. Further, the particle size distribution of the solid in the slurry was investigated by a Coulter counter method, whereby the average particle size was found to be 0.7 μm.

The slurry thus obtained was treated by a disperser for 30 minutes and then spray-dried by means of a spray drier provided with a high speed rotary disk, whereby a fine powder solid (Precursory oxide) was obtained. The spray-drying was conducted under such condition that the temperature of the gas was 360° C. at the inlet and from 150° to 160° C. at the outlet. The particle size of the fine powder solid thereby obtained was within a range of from about 5 to about 50 μm. The strength was low and it was found to be suitable for the subsequent step. Further, the P/V atomic ratio of this fine powder was 1.05.

(B) Preparation of the second component

In 60 kg of deionized water, 6.929 kg of 85% phosphoric acid and 5.987 kg of oxalic acid ($H_2C_2O_4.2H_2O$) were added and dissolved under stirring and heating to 80° C. While paying a careful attention to the generation of bubbles, 4.319 kg of vanadium pentoxide was gradually added and dissolved, and the solution was cooled. Water was added to bring the total amount of the solution to 82.8 kg. The P/V atomic ratio of this solution was 1.266 and the solution contained 0.5 mol of oxalic acid per gram atom of vanadium. Further, this solution was stable and no precipitation of solid took place even when stored at room temperature for 1 month.

(C) Preparation of a catalyst composition

To 40 kg of the vanadyl phosphate solution prepared as the second component in Example 22 (B), 6.20 kg of a 40% silica sol solution as the third component was added under stirring, and then 3.865 kg of the fine powder solid obtained as the first component in Example 22 (A) was added. This slurry was treated by a continuous wet-type mill to obtain a sufficiently uniform slurry. The slurry was spray-dried by means of spray-drier. The solid concentration of the slurry was 20%, and the temperature of the gas was 210° C. at the inlet and 130° C. at the outlet. The solid particles thus obtained had an average particle size of 61 μm and had satisfactory sphericity and strength.

The solid particles were calcined at 500° C. for 2 hours in a nitrogen stream to obtain a catalyst composition. The X-ray diffraction peaks of this catalyst composition were the same as the X-ray diffraction peaks shown in Table B, thus indicating that a calcined oxide [$(VO)_2P_2O_7$ crystal phase] was formed. Further, the intensity of the X-ray diffraction peaks was substantially the same as the intensity expected from the amount of the precursory oxide used in the preparation of the catalyst composition. Thus, it is considered that in the process for the preparation of the catalyst composition, the crystal phase of the precursory oxide prepared by the hydrothermal treatment in the process for the preparation of the above first component was entirely transformed into the crystal phase of the calcined oxide and no conversion of the vanadyl phosphate solution used as a binder to the calcined oxide took place.

EXAMPLE 23

(A) Preparation of the first component (Calcined oxide)

The fine powder solid obtained in Example 22 (A) was divided and placed in porcelain dishes having a capacity of 2 l and then calcined in a muffle furnace. The interior of the furnace was flushed with nitrogen prior to the temperature rise, and maintained at a temperature of 500° C. for 2 hours while supplying nitrogen. Then, air was gradually introduced and the temperature was maintained at 500° C. for further 1 hour and then lowered whereby the first compoent (Calcined oxide) was obtained. The X-ray diffraction peaks of the calcined oxide were the same as the X-ray diffraction peaks shown in Table B, thus indicating the conversion to a $(VO)_2P_2O_7$ crystal phase.

(C) Preparation of a catalyst composition

A slurry was prepared in the same manner as in Example 22 (C) except that 3.47 kg of the calcined oxide of Example 23 (A) was used. The slurry was spray-dried and calcined to obtain a catalyst composition. The solid particles obtained by the spray-drying had an average particle size of 59 μm and had satisfactory sphericity and strength. Further, the X-ray diffraction peaks of the catalyst composition were substantially the same as those of Example 22.

EXAMPLES 22 AND 23

(D) Reaction Example

Into fluidized bed reactors having an inner diameter of 17 mm, 20 ml of the catalyst compositions obtained in Examples 22 (C) and 23 (C) (particle size; 44 to 116 μm) were respectively introduced, and air containing 3% by volume of n-butane was introduced into the respective reactors at a flow rate of GHSV 500 to carry out the reaction. The products were absorbed in water, and the performance of the reactions was determined by potentiometric titration of the respective aqueous solutions and gas chromtography of the respective exhaust gases. The results thereby obtained are shown in Table 10.

TABLE 10

| Example No. | Optimum reaction temperature | Conversion of n-butane | Yield of maleic anhydride |
|---|---|---|---|
| 22 | 440° C. | 86.1% | 45.4% |
| 23 | 425° C. | 86.5% | 49.5% |

EXAMPLE 24

(A) Preparation of the first component (Precursory oxide)

In a 100 l container with glass lining and provided with a jacket, 24.6 l of deionized water and 14.165 kg of phosphoric acid were mixed, and then 1.73 kg of a 85% hydrazine hydrate solution was added and mixed. Then, while paying a careful attention to the generation of bubbles, 10.635 kg of vanadium pentoxide was gradually added to obtain a uniform blue-colored solution. Thereafter, the temperature of the heating medium was raised, and after confirming the termination of the generation of bubbles, the container was closed. The solution was heated to 140° C. The time required for the temperature rise was about 1.5 hours. The heating was continued for 10 hours at the same temperature to complete the hydrothermal treatment. A small amount of solid was filtered from the slurry, and the light blue precipitates were subjected to an X-ray diffraction measurement, whereby the precipitates were found to show the X-ray diffraction peaks as identified in Table A. From the elemental analysis, the composition of the solid was found to be generally represented by the formula $(V_2O_4)(P_2O_5)(2H_2O)$. This slurry was uniformly mixed and then spray-dried to obtain light blue precursory oxide powder to be used as the first component.

(B) Preparation of the second component

In 5.0 kg of deionized water, 3.50 kg (30.357 mol) of 85% phosphoric acid and 3.025 kg (24 mol) of oxalic acid ($H_2C_2O_4.2H_2O$) were added and dissolved under stirring and heating to 80° C. To this solution, 2.182 kg (12.0 mol) of vanadium pentoxide was gradually added and dissolved while paying a careful attention to the generation of bubbles. After cooling the reaction mixture, water was added to bring the total amount of the solution to 11.85 kg. The P/V atomic ratio in this solution was 1.265, and the concentration of oxides ($V_2O_4+P_2O_5$) was 35% by weight.

(C) Preparation of a catalyst composition (Catalyst No. 21)

0.379 kg of the precursory oxide powder obtained as the first component in Example 24 (A), 1.114 kg of a solution of the second component obtained in Example 24 (B), a solution obtained by diluting 0.675 kg of a 40% colloidal silica sol solution as the third component with 2.911 kg of deionized water and 10 g of calcium hydroxide were mixed, and the mixture was thoroughly admixed by a continuous wet-type pulverizer. Then, the mixture was spray-dried to obtain spherical solid particles having an average particle size of about 60 μm. By means of a quartz tube calcination furnace, 60 g of the solid particles were calcined in a fluidized condition in a nitrogen stream to obtain a catalyst composition (Catalyst No. 21). The calcination was conducted at a temperature of 600° C. for 3 hours. The P/V atomic ratio in the catalyst composition was 1.16.

EXAMPLES 25 TO 29

(A) Preparation of the first components (Calcined oxides)

10 kg of the precursory oxide powder obtained in Example 24 (A) was divided and placed in porcelain dishes having a capacity of 2 l and calcined in a muffle furnace having a capacity of 500 l. The interior of the furnace was purged with nitrogen prior to the temperature rise. The temperature was raised while supplying nitrogen, and the calcination was carried out at 550° C. for 2 hours. Then, air was gradually introduced and the calcination was continued for further 1 hour. The powder thereby obtained was yellowish brown, and the X-ray diffraction peaks of the powder were found to be identical with the X-ray diffraction peaks shown in Table B. The valence of vanadium was measured by an oxidation-reduction titration method, whereby $V^{5+}/\Sigma V$ (the ratio of pentavalent vanadium in the total vanadium) was found to be 23.4%.

(C) (Preparation of catalyst compositions (Catalysts Nos. 22 to 26)

0.340 kg of the first component obtained in the above (A), 1.114 kg of the solution of the second component obtained in Example 24 (B), a solution obtained by diluting 0.675 kg of a 40% colloidal silica solution as the third component with 2.911 kg of deionized water and 10 g of an alkaline earth metal compound shown in Table 10 and used as an activity promoting component, were mixed, and the mixture was thoroughly admixed by a continuous wet-type mill. The mixture was then spray-dried and calcined under the same conditions as in Example 24 (C) to obtain a catalyst composition (Catalyst Nos. 22 to 26). The P/V atomic ratio in the catalyst was 1.16, and the atomic ratio of the alkaline earth metal to vanadium was within a range of from 0.039 to 0.013.

EXAMPLE 30

(C) Preparation of a catalyst composition (Catalyst No. 27)

A catalyst composition (Catalyst No. 27) was prepared in the same manner as in Example 25 (C) except that the addition of 10 g of the alkaline earth metal compound was omitted.

EXAMPLES 24 TO 30

(D) Reaction Example 5 g of each fluidized bed catalyst coomposition obtained in Examples 24 (C) to 30 (C) was pulverized in a porcelain mortar and pelletized into pellets of 5 mm $\phi \times 3$ mm H by a pelletizer. The pellet were crushed to obtain particles having a particle size within a range of from 14 to 24 mesh(JIS). Into a micro reactor made of hard glass and having a diameter of 6 mm, 1 ml of the catalyst was filled, and an air-gas mixture containing 1.5% by volume of n-butane was passed therethrough at a flow rate of GHSV 2000 to carry out the reaction. The product was passed through a gas sampler and directly quantitatively analysed by gas chromatography. The results of the reactions thereby obtained are shown in Table 11.

TABLE 11

| Example No. | Catalyst No. | Additive | Reaction temperature (°C.) | Conversion of n-butane (%) | Yield of maleic anhydride (%) |
|---|---|---|---|---|---|
| 24 | 21 | Ca(OH)$_2$ | 468 | 90.9 | 49.7 |
| 25 | 22 | Mg(OH)$_2$ | 453 | 95.1 | 57.9 |
| 26 | 23 | Ca(OH)$_2$ | 452 | 92.8 | 55.2 |
| 27 | 24 | Sr(OH)$_2$ | 455 | 92.0 | 53.0 |
| 28 | 25 | Ba(OH)$_2$ | 463 | 91.9 | 52.8 |
| 29 | 26 | CaSiO$_3$.xH$_2$O | 462 | 89.4 | 54.0 |
| 30 | 27 | — | 480 | 93.2 | 49.9 |

EXAMPLE 31

(A) Preparation of the first component (Precursory oxide)

Into a 100 l pressure container with glass lining and provided with a jacket, 38.0 kg of deionized water, 21.83 kg of 85% phosphoric acid and 2.85 kg of a 80% hydrazine hydrate solution were fed. Then, while paying a careful attention to the generation of bubbles, 16.40 kg of vanadium pentoxide powder was gradually added and dissolved under stirring. During this period, a cooling medium was circulated in the jacket to control the temperature rise due to the exothermal reaction and to maintain the temperature of the solution at a level of from 60° to 80° C. The addition of vanadium pentoxide was completed in about 4 hours, whereby a blue-colored vanadyl phosphate solution was obtained. To this solution, 1.0 kg of seed crystals were added, and then the solution was heated by circulating a hot medium heated to 160° C. in the jacket. The temperature of the solution was raised to 140° C. in 2 hours, the hydrothermal treatment was continued for 10 hours at the same temperature. During this period, the pressure was about 2.4 kg/cm$^2$G. After cooling the reaction mixture to 90° C., 10.3 kg of deionized water was added to adjust the solid content in the slurry to about 35% and then the slurry was withdrawn. The solid thereby obtained was subjected to an X-ray diffraction measurement, whereby the solid was found to show the characteristic X-ray diffraction peaks as identified in Table A and thus it was confirmed to be a pure precursory oxide. Further, the particle size distribution of the solid in the slurry was investigated by a Coulter counter method, whereby the average particle size was found to be 0.7 μm. This oxide slurry was spray-dried by means of a spray-drier to obtain 29.8 kg of a light blue oxide powder. The P/V atomic ratio based on the feed materials of the oxide slurry was 1.05. It was confirmed that the precursory oxide obtained by filtering the sample withdrawn for the measurement of the abovementioned X-ray diffraction measurement and washing it, can generally be represented by the formula (V$_2$O$_4$) (P$_2$O$_5$) (2H$_2$O).

(B) Preparation of the second component

As an example of a starting material suitable for an amorphous complex oxide containing phosphorus and vanadium as the major constituents, a vanadyl phosphate solution was prepared. In 3.0 kg of deionized water, 2.956 kg of 85% phosphoric acid was dissolved, and 2.55 kg of oxalic acid (H$_2$C$_2$O$_4$.2H$_2$O) was further added and dissolved under heating. The solution was heated to 80° C., and 1.842 kg of vanadium pentoxide was gradually added and dissolved while paying a careful attention to the generation of bubbles. Then, the heating was continued for further 10 minutes under the boiling condition to complete the reduction. The solution was cooled, and deionized water was added to adjust the total amount to 10.00 kg, whereby the second component was obtained.

(C) Preparation of a catalyst composition (Catalyst No. 31)

393.6 g of the dried powder of the precursory oxide obtained in Example 31 (A), 1.143 kg of the vanadyl phosphate solution obtained in Example 31 (B) and a solution obtained by diluting 625.1 g of a commercially available 40% colloidal silica solution with 2.84 kg of deionized water, were mixed, and then the mixture was treated by a continuous wet-type pulverizer to obtain a sufficiently uniform slurry. This slurry was spray-dried by means of a spray-drier to obtain spherical solid particles having an average particle size of 58 μm. The solid particles were calcined at a temperature of 350° C. for 1 hour in an air stream and then at 500° C. for 2 hours in a nitrogen stream, whereby a catalyst composition (Catalyst No. 31) was obtained.

EXAMPLE 32

(A) Preparation of the first component (Calcined oxide)

The precursory oxide obtained in Example 31 (A) was calcined to obtain a calcined oxide. Namely, 10 kg of the precursory oxide obtained in Example 31 (A) was divided and placed in 10 procelain dishes having a capacity of 2 l, and the porcelain dishes were placed in a muffle furnace having a capacity of 500 l. After flushing the interior of the furnace with nitrogen gas, the temperature was raised and the calcination was carried out at a temperature of 550° C. for 2 hours. Then, air was gradually introduced into the furnace and the heating was continued for further 1 hour. Then, the furnace was cooled. As a result of the X-ray diffraction measurement, the powder obtained by the calcination was found to show no peaks other than the X-ray diffraction peaks shown in Table B, and thus the powder was confirmed to be a highly pure calcined oxide. Further, the ratio of the pentavalent vanadium in the total vanadium atoms was measured by an oxidation-reduction titration method, whereby it was found to be 23.4%. Namely, it was found that at least part of vanadium in $(VO)_2P_2O_7$ absorbed oxygen and assumed the pentavalent state while maintaining the crystalline structure.

(C) Preparation of a catalyst composition (Catalyst No. 32)

A catalyst composition (Catalyst No. 32) was prepared in the same manner as in Example 31 (C) except that 353.2 g of the calcined oxide powder obtained in Example 32 (A) was used instead of the precursory oxide powder of Example 31 (A).

COMPARATIVE EXAMPLE 1

(C) Preparation of a catalyst composition (Catalyst No. 33)

Without using the calcined oxide powder obtained in Example 32 (A), 1.43 kg of the vanadyl phosphate solution obtained in Example 31 (B), 1.25 kg of a 40% colloidal silica solution and 1.32 kg of deionized water were mixed, and the mixture was sprayed-dried to obtain spherical solid particles having an average particle size of 56 μm. The solid particles were calcined in the same manner as in Example 31 (C) to obtain a catalyst composition (Catalyst No. 33).

EXAMPLES 33 TO 36

(C) Preparation of a catalyst compositions (Catalysts Nos. 34 to 37)

The precursory oxide obtained in Example 31 (A) or the calcined oxide powder obtained in Example 32 (A), the vanadyl phosphate solution obtained in Example 31 (B) and the colloidal silica solution were mixed in the various proportions as shown in Table 12. The mixtures thereby obtained were respectively spray-dried to obtain spherical solid particles, and the solid particles were calcined in the same manner as in Example 31 (C) to obtain catalyst compositions (Catalysts Nos. 34 to 37)

The methods for the preparation of the Catalysts Nos. 31 to 37, their compositions and the results obtained by measuring their physical properties are shown in Tables 12 and 13.

TABLE 12

| | Methods for the Preparation of the Catalysts | | | |
|---|---|---|---|---|
| Catalyst No. | A/B/C* (wt. %) | First component | Spray-drying temperature (°C.)** | Oxide concentration in slurry (wt. %) |
| 31 | 35/40/25 | Precursory oxide | 130 | 20 |
| 32 | 35/40/25 | Calcined oxide | 130 | 20 |
| 33 | 0/50/50 | No addition | 160 | 20 |
| 34 | 60/20/20 | Precursory oxide | 170 | 45 |
| 35 | 45/35/20 | Precursory oxide | 170 | 45 |
| 36 | 12/63/25 | Calcined oxide | 150 | 20 |
| 37 | 35/40/25 | Calcined oxide | 140 | 35 |

*A/B/C: Dry weight ratio of First component/Second component/Third component
**An average temperature of the gas in the chamber

TABLE 13

| | | Compositions and Physical Properties of the Catalysts | | | | | | |
|---|---|---|---|---|---|---|---|---|
| | | Composition | | | Pore volume (ml/g) | | Meso | |
| Exp. No. | Catalyst No. | Content of First component | P/V atomic ratio | Specific surface area (m²/g) | 37–2000Å | 2000–20000Å | pore ratio (%)* | Strength** |
| Exp. 31 | 31 | 35% | 1.16 | 3.9 | 0.043 | 0.016 | 72 | 0.9 |
| Exp. 32 | 32 | 35 | 1.16 | 5.0 | 0.097 | 0.016 | 55 | 1.2 |
| Comp. Exp. 1 | 33 | 0 | 1.27 | 9.9 | 0.070 | 0.006 | 67 | 0.40 |
| Exp. 33 | 34 | 60 | 1.08 | 32.0 | 0.209 | 0.026 | 40 | 31 |

TABLE 13-continued

| | | Compositions and Physical Properties of the Catalysts | | | | | | |
|---|---|---|---|---|---|---|---|---|
| | | Composition | | | Pore volume (ml/g) | | Meso pore | |
| Exp. No. | Catalyst No. | Content of First component | P/V atomic ratio | Specific surface area (m²/g) | 37– 2000Å | 2000– 20000Å | ratio (%)* | Strength** |
| Exp. 34 | 35 | 45 | 1.08 | 21.3 | 0.158 | 0.036 | 30 | 19 |
| Exp. 35 | 36 | 12 | 1.16 | 5.0 | 0.120 | 0.006 | 52 | 2.0 |
| Exp. 36 | 37 | 35 | 1.16 | 8.0 | 0.020 | 0.028 | 34 | 4.2 |

*The ratio (%) of the pores having a pore radius within a range of from 100 to 350 Å in the total pores having a pore radius within a range of from 37 to 2000 Å
**The catalyst composition particles were driven together with air from high velocity nozzles to collide against a metal plate, whereby the destruction loss (%) of the catalyst is measured. The smaller the value, the greater the strength.

EXAMPLES 31 TO 36 AND COMPARATIVE EXAMPLE 1

(D) Reaction Example 1

With use of an air-gas mixture containing 3% by volume of n-butane, an activity test was conducted by means of a small fluidized bed reactor made of hard glass with 20 ml of the catalyst composition and at a flow rate of GHSV 500. The reaction product was absorbed in water, and the quantitative analysis was carried out by potentiometric titration of the aqueous solution and gas chromatography of the exhaust gas. The results thereby obtained are shown in Table 14.

TABLE 14

| Example No. | Catalyst No. | Reaction temperature (°C.) | Conversion of n-butane (%) | Yield of maleic anhydride (%) |
|---|---|---|---|---|
| Exp. 31 | 31 | 440 | 86.1 | 45.4 |
| Exp. 32 | 32 | 425 | 86.5 | 49.5 |
| Comp. Exp. 1 | 33 | 500 | 68.5 | 21.4 |
| Exp. 33 | 34 | 440 | 78.0 | 34.1 |
| Exp. 34 | 35 | 430 | 77.0 | 36.5 |
| Exp. 35 | 36 | 470 | 68.5 | 32.0 |
| Exp. 36 | 37 | 450 | 85.0 | 44.5 |

(D) Reaction Example 2

Each of the Catalysts 32 and 34 and the calcined oxide powder of Example 32 (C) was pulverized in a mortar, and pelletized into pellets of 7 mm $\phi \times 2$ mm H by a pelletizer. The pellets were crushed and sieved to obtain particles having a particle size within a range of from 14 to 24 mesh. In a micro reactor made of hard glass and having a diameter of 6 mm, 1 ml of the particles were filled, an air-gas mixture containing 1.5% by volume of n-butane was reacted at a flow rate of GHSV 2000. The product was analyzed by gas chromatography. The catalytic activities were compared. The results thereby obtained are shown in Table 15.

TABLE 15

| Catalyst No. | Content of First component | Reaction Temperature | Conversion of n-butane | Yield of maleic anhydride |
|---|---|---|---|---|
| 32 | 35% | 462° C. | 94.0% | 54.5% |
| 34 | 60 | 455 | 84.3 | 40.5 |
| Calcined oxide | 100 | 460 | 92.9 | 55.0 |

From the above Table, it is evident that the catalytic activities can not be determined merely by the ratio of the first component. Especially when the ratio of the pores having a pore radius within a range of from 100 to 350 Å is low, the catalyst tends to have a lower catalytic activity.

(D) Reaction Example 3

Into the small fluidized bed reactor used in the above Reaction Example 1, 20 ml of the Catalyst 32 was filled, and an air-gas mixture containing 3% by volume of n-butane and 0.8% by volume of 1-butene was introduced and reacted. At a flow rate of GHSV 500 and at a reaction temperature of 440° C., the conversion of n-butane was 81.3% and the conversion of 1-butene was 100%, and the yield of maleic anhydride relative to the total hydrocarbons was 45.6%.

Further, the gas mixture introduced into the reactor was changed to an air-gas mixture containing 3% by volume of 1-butene and the reaction was carried out in the same manner. At the flow rate of GHSV 500 and at the reaction temperature of 400° C., the conversion of 1-butene was 100%, and the yield of maleic anhydride was 56.0%.

We claim:

1. A process for preparing an oxidation catalyst composition, which comprises:
    (a) mixing, as the first component (i), at least one crystalline composite oxide selected from the group consisting of (1) a crystalline composite oxide containing vanadium and phosphorus having the characteristic X-ray diffraction peaks identified in Table A and (2) a crystalline composite oxide containing vanadium and phosporus having the characteristic X-ray diffraction peaks identified in Table B,

TABLE A

| X-ray diffraction peaks (Anticathode: Cu—K$_\alpha$) 2θ (±0.2°) |
|---|
| 15.7° |
| 19.6° |
| 24.2° |
| 27.1° |
| 28.8° |
| 30.4° |

TABLE B

| X-ray diffraction peaks (Anticathode: Cu—K$_\alpha$) 2θ (±0.2°) |
|---|
| 14.2° |
| 15.7° |
| 18.5° |
| 23.0° |

TABLE B-continued

X-ray diffraction peaks
(Anticathode: Cu—K$_\alpha$)
2θ (±0.2°)

28.4°
30.0°
33.7°
36.8° as the second component (ii), an aqueous solution containing vanadium and phosphorus, and, as the third component (iii), silica sol, thereby forming an aqueous slurry of said components;

(b) spray-drying the slurry; and (c) calcining the solid particles thereby obtained.

2. The process according to claim 1 wherein the second component is an aqueous solution containing vanadyl phosphate.

3. The process according to claim 1 wherein the mixing ratio by dry weight of the first, second and third components is within a range of:

first component:second component:third component = 1:0.1–7:0.05–4.

4. The process according to claim 1 wherein the atomic ratio of phosphorus to vanadium in the oxidation catalyst composition obtained is within a range of from 0.8 to 1.5.

5. The process according to claim 1 wherein the content of the first component in the oxidation catalyst composition obtained is within a range of from 15 to 80% by weight.

6. The process according to claim 1 wherein the first component is a crystalline composite oxide containing vanadium and phosphorus having the characteristic X-ray diffraction peaks as identified in Table A.

7. The process according to claim 6 wherein the first component is a crystalline composite oxide present in an aqueous slurry obtained by the hydrothermal treatment of an aqueous solution containing pentavalent phosphorus and tetravalent vanadium at a temperature of from 110° to 250° C.

8. The process according to claim 6 wherein the first component is a crystalline composite oxide obtained by spray-drying an aqueous slurry obtained by hydrothermal treatment of an aqueous solution containing pentavalent phosphorus and tetravalent vanadium at a temperature of from 110° to 250° C.

9. The process according to claim 6 wherein the first component is a crystalline composite oxide obtained by solid-liquid separation of an aqueous slurry obtained by the hydrothermal treatment of an aqueous solution containing pentavalent phosphorus and tetravalent vanadium at a temperature of from 110° to 250° C., and the second component is an aqueous solution obtained by adding and dissolving phosphoric acid, a reducing agent and vanadium pentoxide in an aqueous solution obtained by the solid-liquid separation.

10. The process according to claim 6 wherein the second component is an aqueous solution containing vanadyl phosphate.

11. The process according to claim 1 wherein the first component is a crystalline composite oxide containing vanadium and phosphorus and showing the characteristic X-ray diffraction peaks as identified in Table B.

12. The process according to claim 11 wherein the first component is a crystalline composite oxide obtained by calcining solid particles obtained by spray-drying an aqueous slurry obtained by the hydrothermal treatment of an aqueous solution containing pentavalent phosphorus and tetravalent vanadium at a temperature of from 110° to 250° C.

13. The process according to claim 11 wherein the first component is a crystalline composite oxide obtained by calcining solid particles obtained by solid-liquid separation of an aqueous slurry obtained by the hydrothermal treatment of an aqueous solution containing pentavalent phosphorus and tetravalent vanadium at a temperature of from 110° to 250° C., and the second component is an aqueous solution obtained by adding and dissolving phosphoric acid, a reducing agent and vanadium pentoxide in an aqueous solution obtained by the solid-liquid separation.

14. The process according to claim 11 wherein the second component is an aqueous solution containing vanadyl phosphate.

* * * * *